(12) United States Patent
Gutterman

(10) Patent No.: US 11,051,443 B1
(45) Date of Patent: Jul. 6, 2021

(54) METHODS AND DEVICES FOR A SEED GERMINATION PROFILE INDICATOR BASED ON ELECTRICAL CONDUCTIVITY

(71) Applicant: Se-cure Pharmaceuticals Ltd, Airport City (IL)

(72) Inventor: Ron Gutterman, Kfar Daniel (IL)

(73) Assignee: Se-cure Pharmaceuticals Ltd, Airport (IL)

( * ) Notice: Subject to any disclaimer, the term of this patent is extended or adjusted under 35 U.S.C. 154(b) by 27 days.

(21) Appl. No.: 16/726,901

(22) Filed: Dec. 25, 2019

(51) Int. Cl.
| | |
|---|---|
| G01N 33/15 | (2006.01) |
| A01C 1/02 | (2006.01) |
| G01N 33/00 | (2006.01) |
| A01G 22/40 | (2018.01) |
| G01N 30/02 | (2006.01) |
| G16C 60/00 | (2019.01) |

(52) U.S. Cl.
CPC ......... *A01C 1/025* (2013.01); *G01N 33/0098* (2013.01); *A01G 22/40* (2018.02); *G01N 2030/027* (2013.01); *G16C 60/00* (2019.02)

(58) Field of Classification Search
CPC .................................................. G01N 33/15
USPC .................................................. 436/20, 150
See application file for complete search history.

(56) References Cited

U.S. PATENT DOCUMENTS

| | | | | |
|---|---|---|---|---|
| 4,230,983 A | * | 10/1980 | Steere | G01N 27/06 324/71.1 |
| 4,975,364 A | * | 12/1990 | Taylor | A01C 1/025 435/29 |
| 5,901,237 A | | 5/1999 | Conrad | |

(Continued)

FOREIGN PATENT DOCUMENTS

EP  3690440  * 8/2020

OTHER PUBLICATIONS

Abdel Samad, I. M. et al, Journal of Experimental Botany 1978, 29, 1471-1478.*

(Continued)

*Primary Examiner* — Arlen Soderquist
(74) *Attorney, Agent, or Firm* — Reuven K. Mouallem; FlashPoint IP Ltd.

(57) ABSTRACT

The present invention discloses methods and devices for a germination profile indicator based on conductivity including: utilizing a target-profile correlation of a target profile of an API from a plant seed to a target germination stage, the target profile includes identifying characteristics of chemical components, and wherein the target germination stage relates to a progress of a seed-germination process of the target profile; utilizing a process-profile correlation of germination-process profiles during the seed-germination process to respective process germination stages, wherein each germination-process profile relates to extracted seed material during the respective process germination stage; comparing characteristics of the target profile to corresponding features in the germination-process profiles; selecting an optimal state of the respective process germination stage to maximize an API quantity; and cross-correlating the optimal state to a conductivity range for the seed in a soak water within a given temperature range to identify a temperature-dependent germination stopping condition.

15 Claims, 3 Drawing Sheets

Exemplary Embodiment

(56) References Cited

U.S. PATENT DOCUMENTS

| | | | | |
|---|---|---|---|---|
| 2003/0147980 A1* | 8/2003 | Wallace | ............... | C07D 311/38 424/757 |
| 2005/0209313 A1* | 9/2005 | Wallace | ............... | C07D 311/38 514/456 |

OTHER PUBLICATIONS

Duke, S. H. et al, Plamt Physiology 1983, 72, 919-924.*
Lu, A. E. et al, 2015 IEEE Conference on Control Applications (CCA) 2015, 1505-1515.*
Khang, D. T. et al, Foods 2016, 5, paper 27, 10 pages.*
Lu, A. E. et al, 2016 American Control Conference (ACC) 2016, 1741-1746.*
Hong, M. S. et al, Computersand Chemical Engineering 2018, 110, 106-114.*
Bagheri, F. et al, Iranian Journal of Pharmaceutical Research 2018, 17, 495-504.*
Cui, M. et al, Analytical and Bioanalytical Chemistry 2019, 411, 3091-3101.*
Lazer, Simona-Laura et al, "Germination and electrical conductivity tests on artificially aged seed lots of 2 wall-rocket species", Turkish Journal of Agriculture (continued) and Forestry, vol. 38 (2014), pp. 857-864, TR.
Genkins, Garet, EPO Examiner, "Extended European Search Report" for EPO Patent Application 20155562, EPO application entitled: (continued) "Methods and Devices for a Seed Germination Profile Indicator Based Onelectrical Conductivity"; European Patent Office, dated May 19, 2020, The Hague.
Genkins, Garet, EPO Examiner, Form1507 for "Extended European Search Report" for EPO Patent Application 20155562, EPO application entitled: (continued) "Methods and Devices for a Seed Germination Profile Indicator Based Onelectrical Conductivity"; European Patent Office, dated May 19, 2020, The Hague.

* cited by examiner

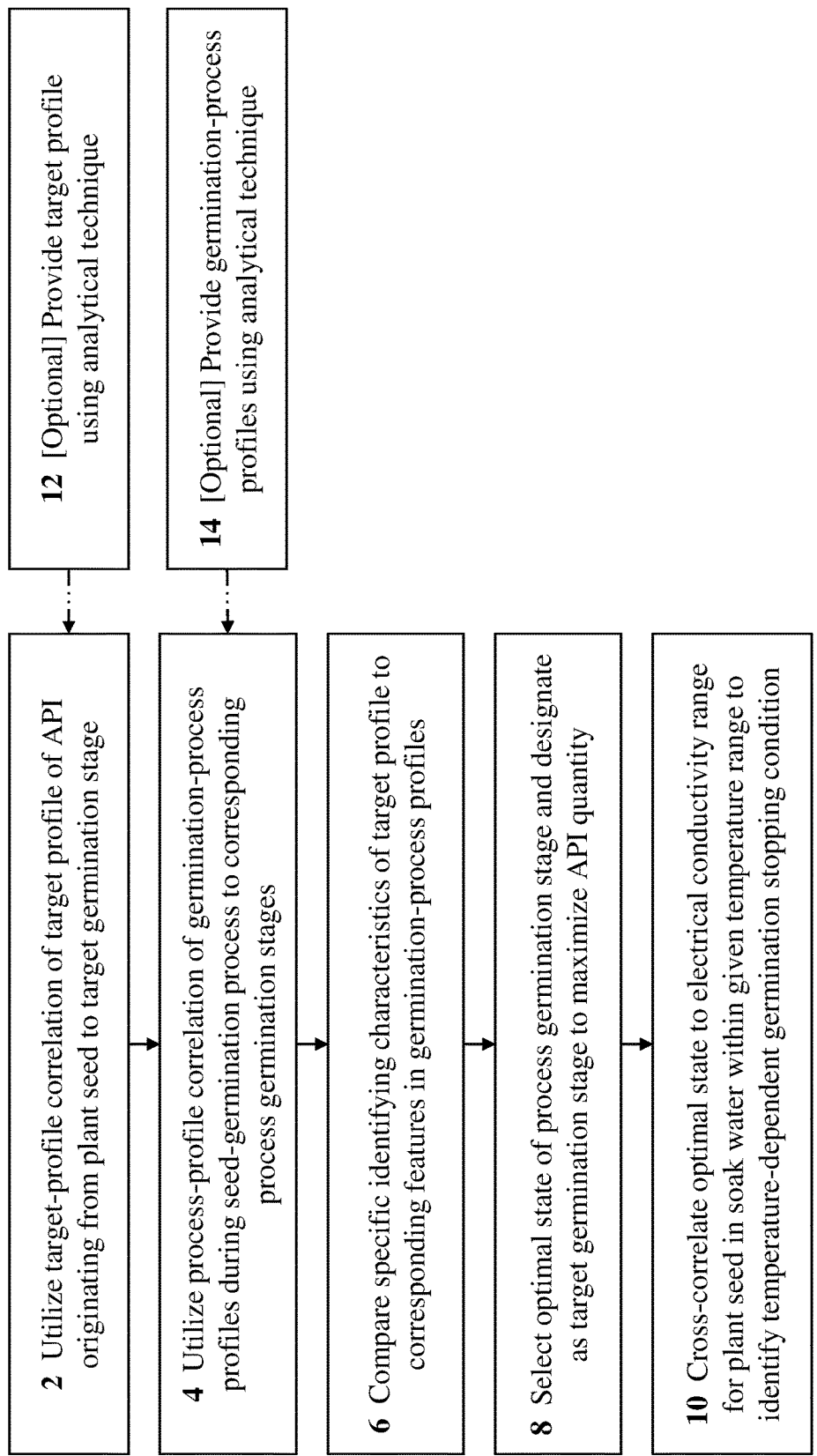

METHODS AND DEVICES FOR A SEED GERMINATION PROFILE INDICATOR BASED ON ELECTRICAL CONDUCTIVITY

FIELD AND BACKGROUND OF THE INVENTION

The present invention relates to methods and devices for a seed germination profile indicator based on electrical conductivity.

Germination in laboratory practice is defined by the AOSA (Association of Official Seed Analysts) as "the emergence and development from the seed embryo of those essential structures, which, for the kinds of seed in question, are indicative of the ability to produce a normal plant under favorable conditions."

The process of seed germination is dramatically influenced by its environment. Such an effect finds expression in both the rate of progress that the germination stage contributes to the emergence of the radicle (the embryonic root of the plant), and beyond germination to sprouting plant growth. Identifying the various stages of germination is a very important goal in agritech processes, broader biochemical processes, derivative processes, and those pertaining to the pharmaceutical industry.

During the germination process, seeds release material that reflects changes in the biochemical processes accompanying germination, with such changes centered on providing a nutrient source during the first stage of germination, albeit transient in nature as subsequent changes occur. In the process of such germination transformation, properties of the volume of water that such seeds are soaking in (hereinafter referred to as soak water) also undergo characteristic changes. In particular, the electrical conductivity of such soak water has been shown to be correlated to aspects of seed development and viability.

In the prior art, U.S. Pat. No. 5,659,623 by Conrad teaches methods for assessing the quality of a seed lot utilizing, inter alia, conductivity tests that measure soak-water conductivity. Correlation was made to low vigor seeds having a poor and leaky membrane structure. Seeds with such a poor membrane structure frequently lose electrolytes, such as amino acids and organic acids, when they imbibe water, thereby increasing the conductivity of the soak water. Other examples of such established tests can be found in the scientific literature such as "Electrical Conductivity Vigour Test: Physiological Basis and Use," Matthews and Powell, *Seed Testing International*, No. 131, pp. 32-35, April 2006 and "Seed-borne pathogens and electrical conductivity of soybean seeds," Wain-Tassi et al., *Sci. Agric.*, v. 69, n. 1, pp. 19-25, January/February 2012.

DT56a (Femarelle®) is a proprietary, non-hormonal API (Active Pharmaceutical Ingredient) derived from the soybean plant that has been shown to act as a novel SERM (Selective Estrogen Receptor Modulator) in the alleviation of menopausal symptoms and prevention of postmenopausal bone loss, without effecting the reproductive tissues of the endometrium and the breast tissue, and without changing the hormonal blood profile.

SC012 (Brizo®) is a proprietary API derived from the soybean plant that has been shown to provide relief for men suffering from irritable lower urinary tract symptoms associated with the benign enlargement of the prostate gland (BPH—Benign Prostate Hyperplasia). SC012 selectively targets the androgen and estrogen receptors within the prostate alone, decreasing the prostate size, thereby relieving the pressure on the urethra from the first month of use without exposing men to unnecessary risks such as impotency.

The production processes for DT65a and SC012 begin with a temperature-controlled vat of soybeans in soak water. During seed germination, the material undergoes biochemical changes for biological nourishing the active germination stage and the development of the plant. The components present in the DT65a and SC012 materials are based on substances that are found at a particular stage in the germination process. The entire germination process for soybeans, for example, is temperature dependent occurs over the span of a few hours, while aforementioned stage in which the desired components occur are transient, lasting only a few minutes up to half an hour.

The challenge is to identify the stage in which the desired components are found in high concentration under varying conditions of temperature and time without having to sample the seeds (i.e., soybeans being legumes) to analyze the components within the seeds for every germination batch.

It would be desirable to have methods and devices for a seed germination profile indicator based on electrical conductivity. Such methods and devices would, inter alia, overcome the various limitations mentioned above.

SUMMARY

It is the purpose of the present invention to provide methods and devices for a seed germination profile indicator based on electrical conductivity.

It is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

Embodiments of the present invention enable the identification of the germination stage of seeds in bulk quantities in a non-invasive way by correlating the chemical profile of transient components during the germination process to the electrical conductivity of the soak water. The process can be temperature-controlled as well as adjusted to calibration to account for variance in seasonal ambient temperature of the industrial soak vats in uncontrolled temperature environments. With such information available in near real-time during the germination process, biochemical changes can be stopped in order to "harvest" the desired components at their maximum concentration.

Therefore, according to the present invention, there is provided for the first time a method for a seed germination profile indicator based on electrical conductivity, the method including the steps of: (a) utilizing a target-profile correlation of a target profile of an active pharmaceutical ingredient (API) originating from a plant seed to a target germination stage, wherein the target profile includes at least one specific identifying characteristic of at least one requisite chemical component, and wherein the target germination stage relates to a progress point of a seed-germination process at which the target profile corresponds; (b) utilizing a process-profile correlation of at least one germination-process profile during the seed-germination process to a respective process germination stage, wherein each at least one germination-process profile relates to extracted seed material from the plant seed during the respective process germination stage, wherein each at least one germination-process profile includes at least one specific identifying characteristic of at least one requisite chemical component, and wherein the respective process germination stage relates to a progress point of the germination progress at which at least one germination-process profile corresponds; (c) comparing at least one specific identifying characteristic of the target profile to corresponding features in at least one germination-process profile; (d) selecting an optimal state of the respective process germination stage, based on the step of comparing, to designate the optimal state as the target germination stage in order to maximize an API quantity; and (e) cross-correlating the optimal state to an electrical conductivity range for the plant seed in a soak water within a given temperature range to identify a temperature-dependent germination stopping condition.

Alternatively, the step of utilizing the target-profile correlation is performed by providing the target profile using an analytical technique, and wherein the step of utilizing the process-profile correlation is performed by providing at least one germination-process profile using an analytical technique.

Most alternatively, the analytical technique is High-Pressure Liquid Chromatography (HPLC).

Alternatively, at least one requisite chemical component is a derivative of the API or a precursor of the API.

Alternatively, the plant seed is a soybean.

According to the present invention, there is provided for the first time a device for a seed germination profile indicator based on electrical conductivity, the device including: (a) a CPU for performing computational operations; (b) a memory module for storing data; (c) an electrical-conductivity module for retrieving electrical-conductivity data; (d) a temperature-sensor module for retrieving temperature data; (e) a germination-profile module configured for: (i) utilizing a target-profile correlation of a target profile of an active pharmaceutical ingredient (API) originating from a plant seed to a target germination stage, wherein the target profile includes at least one specific identifying characteristic of at least one requisite chemical component, and wherein the target germination stage relates to a progress point of a seed-germination process at which the target profile corresponds; and (ii) utilizing a process-profile correlation of at least one germination-process profile during the seed-germination process to a respective process germination stage, wherein each at least one germination-process profile relates to extracted seed material from the plant seed during the respective process germination stage, wherein each at least one germination-process profile includes at least one specific identifying characteristic of at least one requisite chemical component, and wherein the respective process germination stage relates to a progress point of said germination progress at which at least one germination-process profile corresponds; (f) a comparator module configured for: (i) comparing at least one specific identifying characteristic of the target profile to corresponding features in at least one germination-process profile; and (ii) selecting an optimal state of the respective process germination stage, based on the comparing, to designate the optimal state as the target germination stage in order to maximize an API quantity; and (g) a conductivity cross-correlation module configured for cross-correlating the optimal state to an electrical conductivity range for the plant seed in a soak water within a given temperature range to identify a temperature-dependent germination stopping condition.

Alternatively, the utilizing the target-profile correlation is performed by obtaining the target profile using an analytical technique, and wherein the utilizing the process-profile correlation is performed by obtaining at least one germination-process profile using an analytical technique.

Most alternatively, the analytical technique is High-Pressure Liquid Chromatography (HPLC).

Alternatively, the at least one requisite chemical component is a derivative of the API or a precursor of the API.

Alternatively, the plant seed is a soybean.

According to the present invention, there is provided for the first time a non-transitory computer-readable storage medium, having computer-readable code embodied on the non-transitory computer-readable storage medium, for a seed germination profile indicator based on electrical conductivity, the computer-readable code including: (a) program code for utilizing a target-profile correlation of a target profile of an active pharmaceutical ingredient (API) originating from a plant seed to a target germination stage, wherein the target profile includes at least one specific identifying characteristic of at least one requisite chemical component, and wherein the target germination stage relates to a progress point of a seed-germination process at which the target profile corresponds; (b) program code for utilizing a process-profile correlation of at least one germination-process profile during the seed-germination process to a respective process germination stage, wherein each at least one germination-process profile relates to extracted seed material from the plant seed during the respective process germination stage, wherein each at least one germination-process profile includes at least one specific identifying characteristic of at least one requisite chemical component, and wherein the respective process germination stage relates to a progress point of the germination progress at which at least one germination-process profile corresponds; (c) program code for comparing at least one specific identifying characteristic of the target profile to corresponding features in at least one germination-process profile; (d) program code for selecting an optimal state of the respective process germination stage, based on the comparing, to designate the optimal state as the target germination stage in order to maximize an API quantity; and (e) program code for cross-correlating the optimal state to an electrical conductivity range for the plant seed in a soak water within a given temperature range to identify a temperature-dependent germination stopping condition.

Alternatively, the program code for utilizing the target-profile correlation is performed by obtaining the target profile using an analytical technique, and wherein the program code for utilizing the process-profile correlation is performed by obtaining at least one germination-process profile using an analytical technique.

Most alternatively, the analytical technique is High-Pressure Liquid Chromatography (HPLC).

Alternatively, at least one requisite chemical component is a derivative of the API or a precursor of the API.

Alternatively, the plant seed is a soybean.

These and further embodiments will be apparent from the detailed description and examples that follow.

BRIEF DESCRIPTION OF THE DRAWINGS

The present invention is herein described, by way of example only, with reference to the accompanying drawings, wherein:

FIG. 3 is a simplified flowchart of the major process steps for a seed germination profile indicator based on electrical conductivity, according to embodiments of the present invention.

DESCRIPTION OF THE ILLUSTRATIVE EMBODIMENTS

Figure 1:
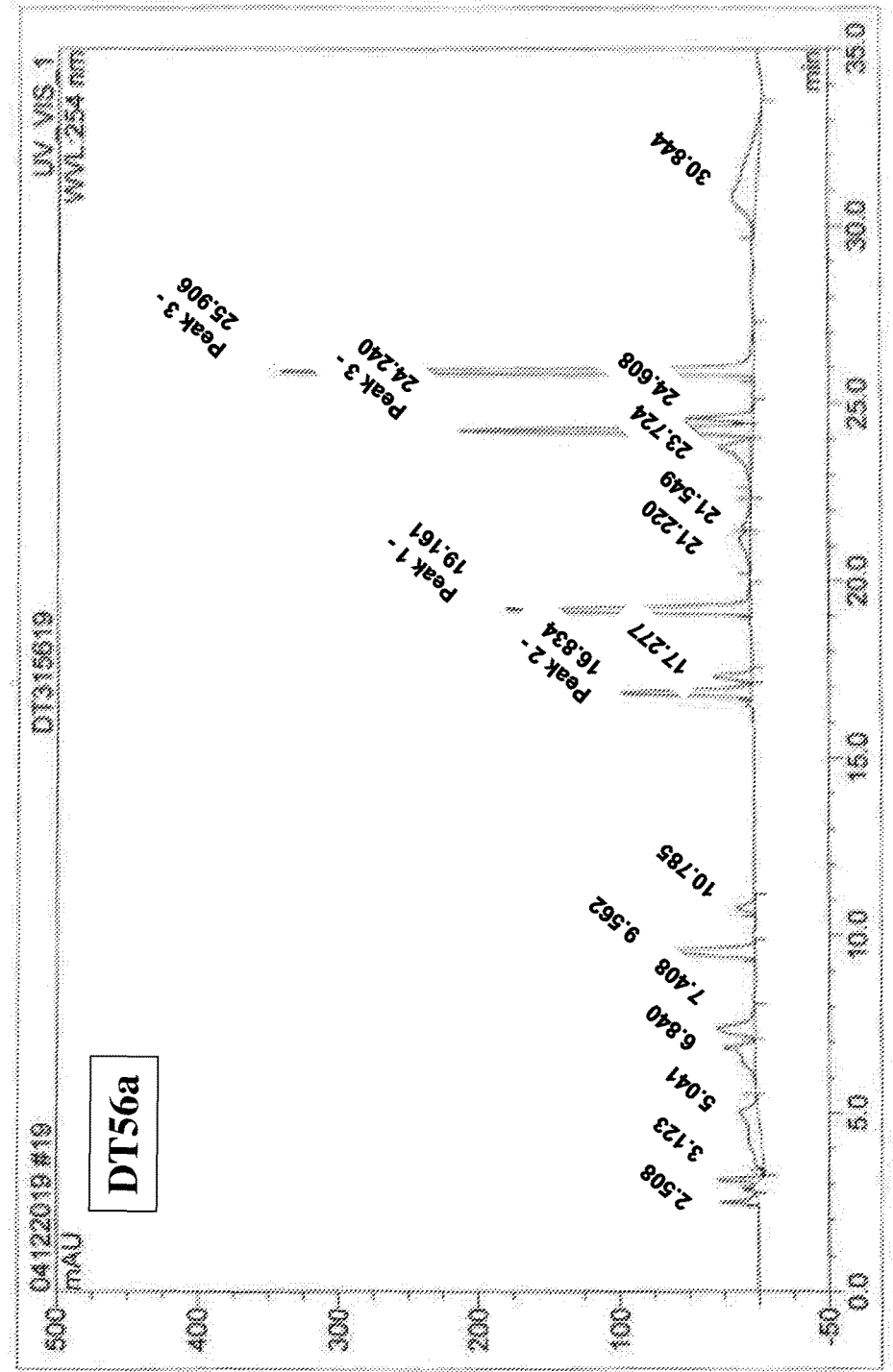
FIG. 1 is an HPLC fingerprint chromatogram of a DT56a sample for an exemplary embodiment depicting the chromatographic separation of extracted seed material from soybeans at a given stage of germination, according to embodiments of the present invention.

The present invention relates to methods and devices for a seed germination profile indicator based on electrical conductivity. The principles and operation for providing such methods and devices, according to the present invention, may be better understood with reference to the accompanying description and the drawings.

The sprouting process of soybeans begins with water absorption into the seed, which initiates the biochemical processes involved in germination, starting the transition from a process of preservation of genetic material and botanical nutrients to the process of germination. The initial water penetration occurs through the hilum (i.e., the "eye" of the soybean seed, which is the point of attachment of the seed to its pod), proceeding with the absorption of water into the skin of the seed (or bean), turning the skin into a supple material. Such flexibility enables bi-directional diffusion through the skin, and thus is the feature that allows components in the seed to be released into the soak water.

Some of the substances released into the soak water are minerals that directly change the conductivity of the soak water, while other released substances indirectly affect soak-water conductivity. As a general rule, a direct correlation between the germination components and the quantity and quality of substances in the soak water can be established.

Inside temperature-controlled germination vats, the conductivity measurement of the soak water is checked at five-minute intervals to determine the level of conductivity corresponding to the stage of seed germination. Such capability allows a user to identify the germination stage in which the necessary transitions in seed material to the desired components has occurred for obtaining the active DT56a and SC012 materials. When the desired germination stage is identified, High-Pressure Liquid Chromatography (HPLC) was performed on samples of the extracted seed material in their final-product API form. At any point during the monitoring of conductivity, the germination process can be terminated in order to isolate the transient biochemical components present at a given stage of germination.

It is important to emphasize that such an indicator technique is not limited to the use of HPLC. Rather, any analytical technique for obtaining a "signature" or "fingerprint" profile of the chemical components present in an API can be employed to obtain a target profile that serves as the basis for developing a cross-correlation conductivity test indicator.

It is noted that typical germination vats can contain hundreds of kilograms of seeds. Requiring analysis of such sizable batches is impractical, while using vat samples of the seeds can introduce unacceptable inconsistency and error into the measurements. Thus, a non-invasive germination profile indicator that factors in the entire contents of a germination vat such as the one described herein mitigates such issues, providing reliability, accuracy, efficiency, near real-time turnaround, quality control, and quality assurance.

Analysis of the biochemical composition of extracted seed material into its major components during the germination process is required in order to enable such a test indicator. The identification of the exact time to halt germination, using the soak-water conductivity values as an indicator, enables the desired biochemical components assessed and optimized by correlating the conductivity with an analytical profile extracted sample material. Such chemical profiles contain the components of the germination stage at the time of sampling, enabling the test to pinpoint the materials that are direct products of transformations during the germination stage.

HPLC has advanced to routinely enable the analysis of chemical components such as amino acids with high accuracy. The capability of mobile-phase gradient elution to separate amino-acid analytes on a chromatographic column is well known.

DT56a and SC012 samples, which are soybean extracts, were used as the reference materials for the desired characteristic profiles to base the correlations on for the conductivity test indicators. Initial sample preparation involved the samples being ground to pass through a 20-mesh sieve (i.e., <0.5 mm powder), checked using a quality control system for sample approval, and stored at dry-room temperatures (e.g., generally between about 18° C. to 24° C., at relative humidity setpoint as low as 0.5%, or room dewpoint setting of about −37° C.). It is noted that DT56a and SC012 don't contain any additional substances such as additives, colorants, odorants, flavorants, and/or preservatives.

HPLC-UV analysis was used to separately determine the DT56a and SC012 biomarkers in the samples which form the foundation of the germination profiles. All analyses on the DT56a and SC012 samples were performed separately and independently. Sample processing involved the biomarkers being extracted into the HPLC column using a methanol solution (HPLC gradient-grade methanol in doubly-distilled water (DDW)) that was injected into the HPLC apparatus (Dionex HPLC 1100 series) equipped with a UV-Vis detector (254 nm).

Chromatographic separation was carried out using a reversed-phase HPLC column via: a linear aqueous methanol gradient elution, a PTFE syringe filter (13 mm diameter, 0.45 μm pore size), an HPLC column (LiChroCART® 4.6-250 mm ID, Purospher® STAR RP-18 endcapped (5 μm)), and a pre-column (LiChroCART 4-4 HPLC guard column, RP-18e (5 μm)).

Sample preparation involved methanol being added to test-tubes containing accurate measures of the samples. The methanol solutions were stirred for 24 hours at room temperature in a rotator. After standing for approximately 15 min. until the upper solution in the test tubes were clear and free of particulate matter, the upper solutions of the sample test tubes were extracted using 1.5-ml Eppendorf pipettes, and transferred to Eppendorf test tubes, which were subsequently placed in a vortex centrifuge at 2400 rpm for one minute. From the centrifuged samples, the upper phases were extracted using 1-ml calibrated syringes. The extracted solutions were then filtered through PTFE syringe filters. The filtered samples were then collected in HPLC vials, loaded into an HPLC autosampler, and injected for analysis.

HPLC analyses were performed at a column temperature of 25° C. using the following injection parameters: a sample volume of 20 μl, a sample temperature of 25° C., a split-loop injection technique, an eluent A of a 10% methanol aqueous solution, and an eluent B of 100% methanol. Table 1 shows the HPLC eluent calibration data.

TABLE 1

HPLC eluent calibration data for eluent A (10% methanol aqueous solution) and eluent B (100% methanol).

| Time (min.) | % A | % B |
|---|---|---|
| 0.00 | 100.0 | 0.0 |
| 20.00 | 43.0 | 57.0 |
| 26.00 | 0.0 | 100.0 |
| 30.00 | 100.0 | 0.0 |
| 35.00 | 100.0 | 0.0 |

Referring to the drawings, FIG. 1 is an HPLC fingerprint chromatogram of a DT56a sample for an exemplary embodiment depicting the chromatographic separation of extracted seed material from soybeans at a given stage of germination for identifying the presence of desired active materials, according to embodiments of the present invention. Peak retention times are indicated in the chromatogram, showing four major peaks based on their mAU intensities (i.e., milli-Absorbance Units) and identified as peaks 1-4 (i.e., the biomarkers of the DT56a sample).

It is noted that while the peaks represent the final-product API components (for those in both FIGS. 1 and 2), the chemical components present at a given stage of germination may or may not be the same as the final product after processing. However, in developing the correlation data for a target profile, it is necessary to establish that the identified peaks that are deemed relevant are responsible for arriving at the final-product components (e.g., precursors or derivatives of the final-product components). Thus, after germination has been interrupted at the desired germination stage, changes may still occur in the component profile due to various post-germination processing. By using samples that have already undergone such post-germination processing as well, any component profile variation due to such processing changes are fully taken into account.

Table 2 shows the profile data of the major identified peaks (P1-P4) of a DT56a sample extracted from soybeans at a given stage of germination with peak height and peak area under the curve (AUC) indicated. Relative height and area are presented as percentages for the ratios of P2 to P1 and P3 to P4, RH and RA respectively.

TABLE 2

HPLC profile data of the major identified peaks (P1-P4) of a DT56a sample extracted from soybeans at a given stage of germination.

| Retention Time (minutes) | Peak Name | Height (mAU) | Relative Height (%) | Area (AUC as mAU × min.) | Relative Area (%) |
|---|---|---|---|---|---|
| 19.16 | 1 | 171.076 | — | 34.398 | — |
| 16.83 | 2 | 94.115 | 55.01 (RH1 = P2/P1) | 16.828 | 48.92 (RA1 = P2/P1) |
| 24.24 | 3 | 210.001 | — | 38.443 | — |
| 25.91 | 4 | 339.582 | 61.84 (RH2 = P3/P4) | 56.683 | 67.82 (RA2 = P3/P4) |

While the exemplary profile data of Table 2 (as well as Table 3 below) utilize RA as the basis for establishing the cross-correlation to conductivity for the test indicator, it is understood that other profile data may be determined more appropriate in order to improve the quality of the correlation depending on the analytical technique employed for obtaining the chemical profile. Thus, AUC could have been simply used as well, without calculating RAs as in Table 2. Likewise, other ratios between the peaks could have been employed. It is assumed that the user interested in developing such a test indicator already has (1) identified an API with associated/intended therapeutic effects, and (2) has further fully identified the target profile associated with the API as the starting point for correlating the target profile to the soak-water conductivity of the seeds of interest containing the API (or derivatives and/or precursors thereof) during the desired germination stage.

In practice, regarding the RAs of Table 2, the continuation of the production process (i.e., whether to allow germination to continue or be halted) depends on the ratio between the amount of desired material preserved in the seed extract and the amount of desired material generated due to the further progress of the germination process. Analysis of the RAs is used to optimize such ratios by comparing the two product peaks (P1 and P3) to two intermediate peaks (P2 and P4) derived from the products.

As mentioned above, it is assumed that in determining the basis for the correlation from the target profile that the features (i.e., the chemical components and their roles in the process of interest) of the target profile are fully understood. Thus, the germination stage needs to be stopped when the reactants in the seeds used to generate the desired products are fully consumed. P1 through P4 were the most stable peaks found from the onset of germination to the final API, and served as reliable markers to identify the desired efficacy profile, as related to pre-clinical models in rats for both DT56a (of FIG. 1 and Table 2 above) and for SC012 (of FIG. 2 and Table 3 below).

Cumulative analysis of a series of HPLC results confirmed that the final product for DT56a exhibited an RA1 in the range of 45.52-79.25% and an RA2 in the range of 55.23-73.3%.

Figure 2:
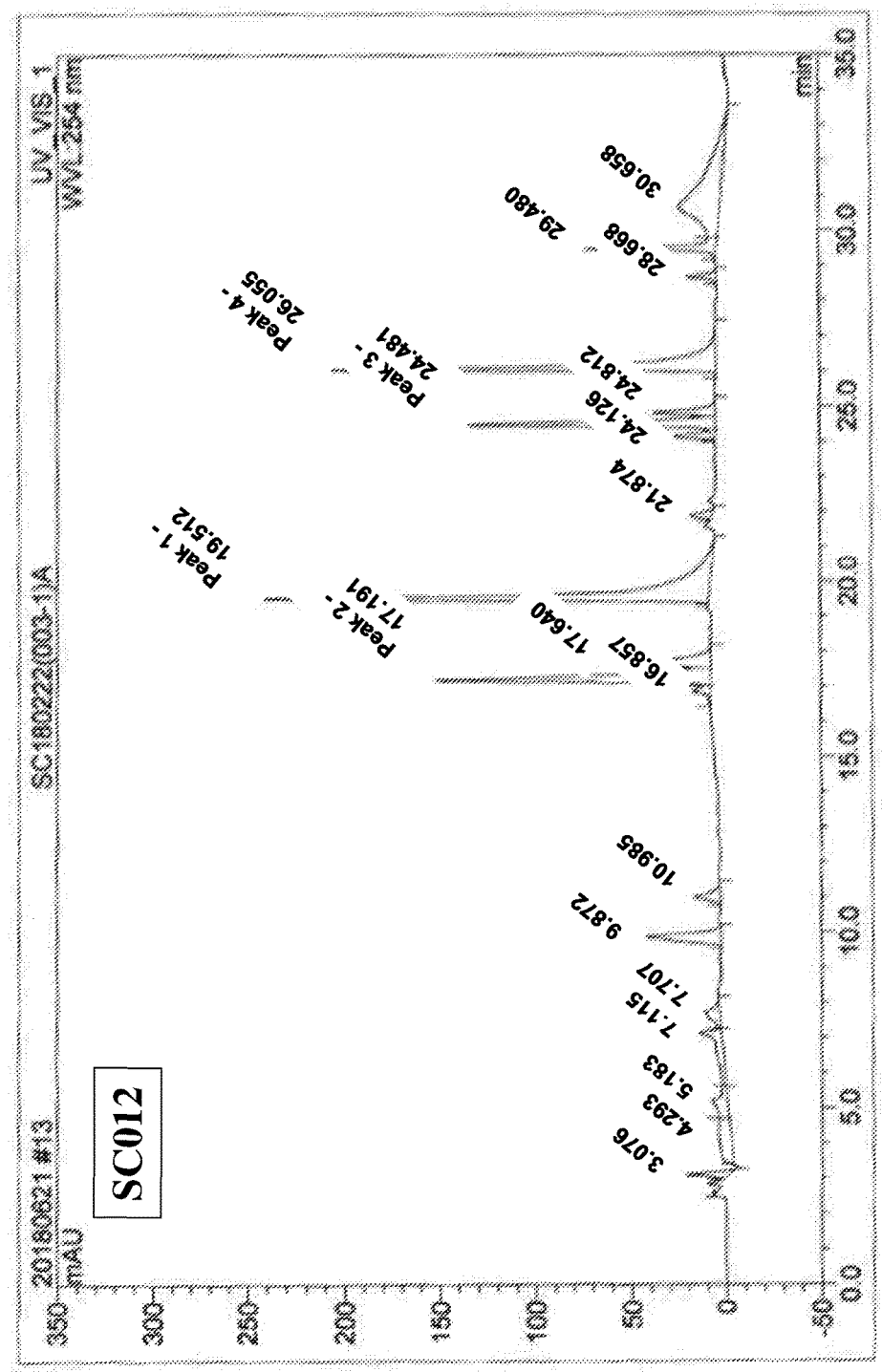
FIG. 2 is an HPLC fingerprint chromatogram of an SC012 sample for an exemplary embodiment depicting the chromatographic separation of extracted seed material from soybeans at a given stage of germination, according to embodiments of the present invention.

FIG. 2 is an HPLC fingerprint chromatogram of an SC012 sample for an exemplary embodiment depicting the chromatographic separation of extracted seed material from soybeans at a given stage of germination for identifying the presence of desired active materials, according to embodiments of the present invention. Peak retention times are indicated in the chromatogram, showing four major peaks based on their mAU intensities (and identified as peaks 1-4 (i.e., the biomarkers of the SC012 sample).

Table 3 shows the profile data of the major identified peaks (P1-P4) of an SC012 sample extracted from soybeans at a given stage of germination with peak height and AUC indicated. Relative height and area are presented as percentages for the ratios of P2 to P1 and P3 to P4, RH and RA respectively.

TABLE 3

HPLC profile data of major identified peaks (P1-P4) of an SC012 sample extracted from soybeans at a given stage of germination.

| Retention Time (minutes) | Peak Name | Height (mAU) | Relative Height (%) | Area (AUC as mAU × min.) | Relative Area (%) |
|---|---|---|---|---|---|
| 19.51 | 1 | 232.631 | — | 54.072 | — |
| 17.19 | 2 | 144.994 | 62.33 (P2/P1) | 28.104 | 51.97 (P2/P1) |
| 24.48 | 3 | 129.681 | — | 21.018 | — |
| 26.05 | 4 | 201.762 | 64.27 (P3/P4) | 36.694 | 57.28 (P3/P4) |

Cumulative analysis of a series of HPLC results confirmed that the final product for SC012 exhibited an RA1 in the range of 50.65-56.22% and an RA2 in the range of 56.2-68.67%.

Electrical conductivity measurements were made of the soak water of seed germination vats in various temperature ranges. Table 4 shows the conductivity ranges (in milliSiemen) at several temperature ranges used to identify a germination stopping value range as a function of the soak-water temperature. The baseline conductivity for the soak water upon initial contact with the seeds at the onset of germination was in the range of 0.72-0.9 mS.

The conductivity ranges were cross-correlated with the desired chemical profiles based on peak-ratio percentages described above in order to determine the desired germination stopping value ranges. These ranges were then used as the basis for obtaining the temperature-dependency of the data shown in Table 4. Such "temperature calibration" of the test indicator allows for precise temperature control to regulate the rate at which the desired germination stage occurs (e.g., to prevent "overshooting" the desired germination stage) as well as variance in seasonal ambient temperature of the industrial soak vats in uncontrolled temperature environments. Such techniques enable a near real-time, non-invasive, conductivity-based determination of the germination stage of bulk quantities of seeds.

TABLE 4

Electrical conductivity measurements of the soak water of seed germination vats in various temperature ranges for employing as a "temperature calibration" for determining germination stopping conditions.

| Temperature (° C.) | Conductivity (mS) |
| --- | --- |
| 18-19 | 3.08-3.32 |
| 20-21 | 3.33-3.45 |
| 22-23 | 3.46-3.59 |
| 24-25 | 3.60-3.87 |
| 26-27 | 3.88-4.19 |
| 28-30 | 4.19-4.51 |

Table 4 provides the germination "stopping" conditions. For example, if it is determined that the window of time for obtaining the desired material (having the representative pre-determined target profile) is too short, the operator may want to lower the temperature of the soak water in the germination vat in order to have better control of terminating the germination process. The operator selects the desired temperature for the soak water, causing the test indicator device to adjust the stopping conductivity range appropriately based on Table 4. In practice, when the stopping conductivity range was reached, the seeds (with their soak water) were ground in the germination vat, causing the germination process to be abruptly halted.

FIG. 3 is a simplified flowchart of the major process steps for a seed germination profile indicator based on electrical conductivity, according to embodiments of the present invention. As mentioned above, it is assumed that information regarding the desired material and its associated/intended use are initially known. The process starts with utilizing a target-profile correlation of a target profile originating from a plant seed to a target germination stage (Step 2). The target profile includes specific identifying characteristics of the chemical components of the API. The target germination stage relates to the point in the seed-germination process at which the target profile corresponds.

The process then utilizes a process-profile correlation of germination-process profiles during the seed-germination process to corresponding process germination stages (Step 4). Each germination-process profile relates to extracted seed material from the plant seed during the corresponding process germination stage. The specific identifying characteristics of the target profile are then compared to corresponding features in the germination-process profiles (Step 6). An optimal state of the process germination stage is then selected and designated as the target germination stage in order to maximize the quantity of the API (Step 8). The optimal state is then cross-correlated to an electrical conductivity range for the plant seed in a soak water within a given temperature range to identify a temperature-dependent germination stopping condition (Step 10).

Optionally, Step 2 of utilizing the target-profile correlation is performed by providing the target profile using an analytical technique (Step 12), and Step 4 of utilizing the process-profile correlation is performed by providing the germination-process profiles using an analytical technique (Step 14).

The general applicability to utilize such techniques for testing a variety of legumes, and more broadly for the full range of seed plants, can be readily understood. The process of seed germination exhibits predictable uniformity across a host of seeds. Seeds in general are characterized as embryonic plants enclosed in protective outer coverings, making them amenable to undergo the same types of maturation processes in soak water as detailed above. Adapting and applying such techniques to other seeds are trivial aspects of employing such a germination profile indicator as explained herein based on electrical conductivity to correlate the chemical profile of transient components during the germination process in a non-invasive way in bulk quantities.

While the present invention has been described with respect to a limited number of embodiments, it will be appreciated that many variations, modifications, and other applications of the present invention may be made.

What is claimed is:

1. A computer-implemented method for a seed germination profile indicator based on electrical conductivity, the method comprising the steps of:
    (a) utilizing a target-profile correlation of a target profile of an active pharmaceutical ingredient (API) originating from a plant seed to a target germination stage, wherein said target profile includes at least one specific identifying characteristic of at least one requisite chemical component, and wherein said target germination stage relates to a progress point of a seed-germination process at which said target profile corresponds;
    (b) utilizing a process-profile correlation of at least one germination-process profile during said seed-germination process to a respective process germination stage, wherein each said at least one germination-process profile relates to extracted seed material from said plant seed during said respective process germination stage, wherein each said at least one germination-process profile includes at least one specific identifying characteristic of at least one requisite chemical component, and wherein said respective process germination stage relates to a progress point of said germination progress at which said at least one germination-process profile corresponds;
    (c) comparing said at least one specific identifying characteristic of said target profile to corresponding features in said at least one germination-process profile;

(d) selecting an optimal state of said respective process germination stage, based on said step of comparing, to designate said optimal state as said target germination stage in order to maximize an API quantity; and (e) cross-correlating said optimal state to an electrical conductivity range for said plant seed in a soak water within a given temperature range to identify a temperature-dependent germination stopping condition.

2. The method of claim 1, wherein said step of utilizing said target-profile correlation is performed by providing said target profile using an analytical technique, and wherein said step of utilizing said process-profile correlation is performed by providing said at least one germination-process profile using an analytical technique.

3. The method of claim 2, wherein said analytical technique is High-Pressure Liquid Chromatography (HPLC).

4. The method of claim 1, wherein said at least one requisite chemical component is a derivative of said API or a precursor of said API.

5. The method of claim 1, wherein said plant seed is a soybean.

6. A device for a seed germination profile indicator based on electrical conductivity, the device comprising:

(a) a CPU for performing computational operations;

(b) a memory module for storing data;

(c) an electrical-conductivity module for retrieving electrical-conductivity data;

(d) a temperature-sensor module for retrieving temperature data;

(e) a germination-profile module configured for:

(i) utilizing a target-profile correlation of a target profile of an active pharmaceutical ingredient (API) originating from a plant seed to a target germination stage, wherein said target profile includes at least one specific identifying characteristic of at least one requisite chemical component, and wherein said target germination stage relates to a progress point of a seed-germination process at which said target profile corresponds; and (ii) utilizing a process-profile correlation of at least one germination-process profile during said seed-germination process to a respective process germination stage, wherein each said at least one germination-process profile relates to extracted seed material from said plant seed during said respective process germination stage, wherein each said at least one germination-process profile includes at least one specific identifying characteristic of at least one requisite chemical component, and wherein said respective process germination stage relates to a progress point of said germination progress at which said at least one germination-process profile corresponds;

(f) a comparator module configured for:

(i) comparing said at least one specific identifying characteristic of said target profile to corresponding features in said at least one germination-process profile; and (ii) selecting an optimal state of said respective process germination stage, based on said comparing, to designate said optimal state as said target germination stage in order to maximize an API quantity; and (g) a conductivity cross-correlation module configured for cross-correlating said optimal state to an electrical conductivity range for said plant seed in a soak water within a given temperature range to identify a temperature-dependent germination stopping condition.

7. The device of claim 6, wherein said utilizing said target-profile correlation is performed by obtaining said target profile using an analytical technique, and wherein said utilizing said process-profile correlation is performed by obtaining said at least one germination-process profile using an analytical technique.

8. The device of claim 7, wherein said analytical technique is High-Pressure Liquid Chromatography (HPLC).

9. The device of claim 6, wherein said at least one requisite chemical component is a derivative of said API or a precursor of said API.

10. The device of claim 6, wherein said plant seed is a soybean.

11. A non-transitory computer-readable storage medium, having computer-readable code embodied on the non-transitory computer-readable storage medium, for a seed germination profile indicator based on electrical conductivity, the computer-readable code comprising:

(a) program code for utilizing a target-profile correlation of a target profile of an active pharmaceutical ingredient (API) originating from a plant seed to a target germination stage, wherein said target profile includes at least one specific identifying characteristic of at least one requisite chemical component, and wherein said target germination stage relates to a progress point of a seed-germination process at which said target profile corresponds;

(b) program code for utilizing a process-profile correlation of at least one germination-process profile during said seed-germination process to a respective process germination stage, wherein each said at least one germination-process profile relates to extracted seed material from said plant seed during said respective process germination stage, wherein each said at least one germination-process profile includes at least one specific identifying characteristic of at least one requisite chemical component, and wherein said respective process germination stage relates to a progress point of said germination progress at which said at least one germination-process profile corresponds;

(c) program code for comparing said at least one specific identifying characteristic of said target profile to corresponding features in said at least one germination-process profile;

(d) program code for selecting an optimal state of said respective process germination stage, based on said comparing, to designate said optimal state as said target germination stage in order to maximize an API quantity; and (e) program code for cross-correlating said optimal state to an electrical conductivity range for said plant seed in a soak water within a given temperature range to identify a temperature-dependent germination stopping condition.

12. The non-transitory computer-readable storage medium of claim 11, wherein said program code for utilizing said target-profile correlation is performed by using data obtained from said target profile using an analytical technique, and wherein said program code for utilizing said process-profile correlation is performed by using data obtained from said at least one germination-process profile using an analytical technique.

13. The non-transitory computer-readable storage medium of claim 12, wherein said analytical technique is High-Pressure Liquid Chromatography (HPLC).

14. The non-transitory computer-readable storage medium of claim 11, wherein said at least one requisite chemical component is a derivative of said API or a precursor of said API.

15. The non-transitory computer-readable storage medium of claim 11, wherein said plant seed is a soybean.

* * * * *